United States Patent
Riondel et al.

(10) Patent No.: US 6,956,130 B2
(45) Date of Patent: Oct. 18, 2005

(54) PROCESS FOR THE MANUFACTURE OF 2-ETHYLHEXYL ACRYLATE

(75) Inventors: Alain Riondel, Forbach (FR); Jacqueline Bessalem, Saint-Avold (FR)

(73) Assignee: Atofina, Puteaux (FR)

( * ) Notice: Subject to any disclaimer, the term of this patent is extended or adjusted under 35 U.S.C. 154(b) by 104 days.

(21) Appl. No.: 10/113,936

(22) Filed: Apr. 2, 2002

(65) Prior Publication Data

US 2002/0183542 A1 Dec. 5, 2002

(30) Foreign Application Priority Data

Apr. 2, 2001 (FR) ............................................. 01.04435

(51) Int. Cl.$^7$ .............................................. C00C 69/52
(52) U.S. Cl. ....................................................... 560/205
(58) Field of Search .......................................... 560/205

(56) References Cited

U.S. PATENT DOCUMENTS

| | | |
|---|---|---|
| 5,093,520 A | 3/1992 | Nestler et al. |
| 5,510,514 A | 4/1996 | Fauconet et al. |
| 5,606,102 A | 2/1997 | Fauconet et al. |
| 6,458,991 B1 * | 10/2002 | Paulus et al. |

* cited by examiner

Primary Examiner—Johann Richter
Assistant Examiner—Paul A. Zucker
(74) Attorney, Agent, or Firm—Miller, White, Zelano, Branigan, P.C.

(57) ABSTRACT

2-Ethylhexyl acrylate is manufactured according to a process for the direct esterification of acrylic acid with 2-ethylhexanol catalysed by sulphuric acid, the acrylic acid subjected to the esterification being stabilized by at least one stabilizing agent, the said esterification being followed by the neutralization by a base of the crude reaction mixture (B1) obtained, the resulting salts passing into the aqueous phase (A1) of the said mixture, the organic phase (O1) and the aqueous phase (A1) resulting from this neutralization being separated and the 2-ethylhexyl acrylate being recovered from the organic phase (O1). To suppress the emulsions which appear during the said neutralization, the stabilizer or stabilizers of acrylic acid is/are chosen with the exclusion of hydroquinone, in the absence of which the aqueous phase of the process is stabilized before and/or during the neutralization.

20 Claims, No Drawings

PROCESS FOR THE MANUFACTURE OF 2-ETHYLHEXYL ACRYLATE

The present invention relates to an improved process for the manufacture of 2-ethylhexyl acrylate by a direct esterification of acrylic acid with 2-ethylhexanol, this reaction being catalysed by sulphuric acid.

In this industrial process, to shift the reaction equilibrium, a solvent which azeotropically entrains the water of reaction is not added but this role is provided by an excess of the esterifying alcohol (in this case, 2-ethylhexanol), which exhibits the distinguishing feature of forming an azeotrope with water.

On conclusion of the reaction stage, which is carried out batchwise, virtually all the sulphuric acid has been converted into 2-ethylhexyl hydrogensulphate (2-EtHexSO$_4$H), according to the following reaction for the esterification of sulphuric acid with 2-ethylhexanol:

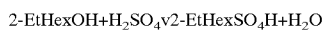

$$2\text{-EtHexOH} + \text{H}_2\text{SO}_4 \rightleftharpoons 2\text{-EtHexSO}_4\text{H} + \text{H}_2\text{O}$$

Consequently, the reaction mixture, at the end of the reaction, comprises 2-ethylhexyl acrylate, 2-ethylhexanol, acrylic acid, 2-ethylhexyl hydrogensulphate, traces of sulphuric acid, and the stabilizers conventionally used in the reaction.

After the esterification reaction, the acidic entities present in the crude reaction mixture are neutralized by addition to the latter of an aqueous solution of a base (sodium hydroxide); during this stage, the acrylic acid is neutralized to sodium acrylate, the 2-ethylhexyl hydrogensulphate to neutral 2-ethylhexyl sulphate (2-EtHexSO$_4$Na) and the traces of sulphuric acid to sodium sulphate Na$_2$SO$_4$, all these salts passing into the aqueous phase. The organic phase and aqueous phase resulting from this neutralization are separated. The desired 2-ethylhexyl acrylate is recovered by distillation from the organic phase and the 2-ethylhexanol is recovered by distillation from the aqueous phase. These purification stages which follow the esterification reaction are generally carried out continuously.

During the implementation of this process for the manufacture of 2-ethylhexyl acrylate, it appears that a dense emulsion is formed at the interphase during the separation by settling which follows the abovementioned neutralization stage. This emulsion, which might be due to 2-ethylhexyl acrylate polymers growing at the interphase, disrupts the downstream distillation line and lowers the environmental performance of the manufacturing plant.

In seeking to solve this problem, the inventors have discovered, surprisingly, that hydroquinone, a stabilizer commonly used for acrylic acid, did not have to be used and that, if it were, at least one specific aqueous-phase stabilizer had to be added in order to avoid the appearance of this emulsion.

International Application PCT WO 98/56746 and U.S. Pat. Nos. 5,928,558 and 5,932,735 disclose, in a general manner, the use of 2,2,6,6-tetramethyl-1-piperidinyloxy (TEMPO) and of its derivatives as stabilizer of (meth)acrylic acid in the presence of water.

A subject-matter of the present invention is therefore first, in the manufacture of 2-ethylhexyl acrylate according to a process for the direct esterification of acrylic acid with 2-ethylhexanol, catalysed by sulphuric acid, the acrylic acid subjected to the esterification being stabilized by at least one stabilizing agent, the said esterification being followed by the neutralization by a base of the crude reaction mixture (B1) obtained, the resulting salts passing into the aqueous phase (A1) of the said mixture, the organic phase (O1) and the aqueous phase (A1) resulting from this neutralization being separated and the 2-ethylhexyl acrylate being recovered from the organic phase (O1), a process for the suppression of the emulsions which appear during the said neutralization, characterized in that the stabilizer or stabilizers of acrylic acid is/are chosen with the exclusion of hydroquinone, in the absence of which the aqueous phase of the process is stabilized before and/or during the neutralization.

Another subject-matter of the present invention is a process for the manufacture of 2-ethylhexyl acrylate by direct esterification of acrylic acid with 2-ethylhexanol in the presence of at least one stabilizer for acrylic acid, the said esterification being catalysed by sulphuric acid, the crude reaction mixture (B1) obtained comprising 2-ethylhexyl acrylate, 2-ethylhexanol, acrylic acid, 2-ethylhexyl hydrogensulphate, traces of sulphuric acid and the usual impurities, following which process the esterification is followed by (a) the addition to the said crude reaction mixture (B1) of a base in order to neutralize the acrylic acid, the 2-ethylhexyl hydrogensulphate and the traces of sulphuric acid which are present therein, the resulting salts passing into the aqueous phase (A1) of the said mixture, the organic phase (O1) and the aqueous phase (A1) resulting from this neutralization being separated and the desired 2-ethylhexyl acrylate being recovered from the organic phase (O1);

(b) the recovery of the 2-ethylhexanol in (A1) from the said aqueous phase, the waste aqueous liquors (E2) freed from the said alcohol being discharged, characterized in that the aqueous phase of the process is stabilized, before or during the neutralization, by the introduction of at least one aqueous-phase stabilizer chosen from metal salts of Fe, Mn and Cu, and 2,2,6,6-tetramethyl-1-piperidinyloxy (TEMPO), 4-hydroxy-2,2,6,6-tetramethyl-1-piperidinyloxy (4-hydroxy-TEMPO), 4-methoxy-2,2,6,6-tetramethyl-1-piperidinyloxy (4-methoxy-TEMPO) and 4-oxo-2,2,6,6-tetramethyl-1-piperidinyloxy (4-oxo-TEMPO).

The metal salts which can be used are chosen in particular from CuSO$_4$, Fe$_2$(SO$_4$)$_3$ and manganese acetate Mn(OAc)$_2$.

The aqueous-phase stabilizer or stabilizers can be introduced into the esterification reactor and/or into the neutralization reactor and/or into a part of the installation situated between these two reactors.

Furthermore, this aqueous-phase stabilizer or these aqueous-phase stabilizers is/are generally introduced in a proportion of 20 to 1000 ppm, in particular from 50 to 200 ppm, with respect to the crude reaction mixture (B1).

The stabilizer or stabilizers of acrylic acid is/are chosen with the exclusion of hydroquinone (HQ) and in particular from phenothiazine (PTZ), hydroquinone methyl ether (HQME), di(tert-butyl)catechol, p-anilinophenol, para-phenylenediamine and their mixtures in all proportions. This stabilizer or these stabilizers can also be chosen from the compounds which have just been listed, hydroquinone and their mixtures in all proportions. The stabilizer or stabilizers of acrylic acid is or are generally present in a proportion of 200 to 2000 ppm with respect to the acrylic acid.

Finally, a subject-matter of the present invention is a process for the manufacture of 2-ethylhexyl acrylate by direct esterification of acrylic acid with 2-ethylhexanol in the presence of at least one stabilizer for acrylic acid, the said esterification being catalysed by sulphuric acid, the crude reaction mixture (B1) obtained comprising 2-ethylhexyl acrylate, 2-ethylhexanol, acrylic acid, 2-ethylhexyl hydrogensulphate, traces of sulphuric acid and the usual impurities, following which process the esterification is followed by (a) the addition to the said crude reaction mixture (B1) of a base in order to neutralize the acrylic acid, the 2-ethylhexyl hydrogensulphate and the traces of sulphuric acid which are present therein, the resulting salts passing into the aqueous phase (A1) of the said mixture, the organic phase (O1) and the aqueous phase (A1) resulting from this neutralization being separated and the desired 2-ethylhexyl acrylate being recovered from the organic phase (O1);

(b) the recovery of the 2-ethylhexanol in (A1) from the said aqueous phase, the waste aqueous liquors (E2) freed from the said alcohol being discharged, characterized in that use is made of one or more stabilizers of acrylic acid chosen from phenothiazine, hydroquinone methyl ether, di(tert-butyl)catechol, p-anilinophenol, para-phenylenediamine and their mixtures in all proportions.

The stabilizer or stabilizers of acrylic acid is or are present in a proportion in particular of 200 to 2000 ppm with respect to the acrylic acid.

The purification which follows the neutralization can be carried out conventionally, by the operations disclosed in European Patent EP-B-609 127.

The entire disclosure[s] of all applications, patents and publications, cited above or below, and of corresponding French Application No. 01.04435, filed Apr. 2, 2001 are hereby incorporated by reference.

EXAMPLES

In the foregoing and in the following examples, all temperatures are set forth uncorrected in degrees Celsius; and, unless otherwise indicated, all parts and percentages are by weight.

The following examples illustrate the present invention without, however, limiting the scope thereof.

Example 1

(Reference)

Acrylic acid is esterified batchwise with 2-ethylhexanol, in the presence of sulphuric acid as catalyst and in the presence of hydroquinone as polymerization inhibitor, in a stirred reactor at 80° C. under reduced pressure.

The crude reaction mixture (B1) thus formed is neutralized to remove the acids present, namely the 2-ethylhexyl hydrogensulphate, the acrylic acid and the traces of sulphuric acid. This neutralization takes place batchwise in another stirred reactor starting from 200 g of crude mixture B1, with a 4% by weight sodium hydroxide solution (time 30 minutes at ambient temperature). The separation by settling is carried out in a separating funnel. In this case, the appearance is recorded of an emulsion at the interphase during the separation by settling.

Examples 2 to 7

(of the Invention)

The same reaction as in Example 1 was carried out with a stabilizer of acrylic acid and an aqueous-phase stabilizer. The results are listed in the following table:

TABLE

| Example | Stabilizer of Acrylic Acid | Aqueous-Phase Stabilizer | Appearance of an emulsion on neutralization |
|---|---|---|---|
| 2 | HQME | — | No |
| 3 | PTZ | — | No |
| 4 | HQ | $CuSO_4$ | No |
| 5 | HQ | $Fe_2(SO_4)_3$ | No |
| 6 | HQ | $Mn(OAc)_2$ | No |
| 7 | HQ | TEMPO | No |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In the manufacture of 2-ethylhexyl acrylate according to a process comprising: direct esterification of acrylic acid with 2-ethylhexanol; catalyzed by sulphuric acid to obtain a crude reaction mixture (B1), the acrylic acid subjected to the esterification being stabilized by at least one stabilizing agent, the esterification being followed by neutralization of the crude reaction mixture (B1) with a base to obtain an organic phase (O1) and an aqueous phase (A1), the resulting salts of the neutralization passing into the aqueous phase (A1), the organic phase (O1) and aqueous phase (A1) being separated and the 2-ethylhexyl acrylate being recovered from the organic phase (O1), wherein the improvement comprises a process for the suppression of the emulsions which appear during the neutralization, which comprises: selecting the stabilizing agent of the acrylic acid during esterification so as to exclude hydroquinone, or, if hydroquinone is contained in the stabilizing agent, stabilizing the aqueous phase before and/or during the neutralization.

2. A process for the manufacture of 2-ethylhexyl acrylate by direct esterification of acrylic acid with 2-ethylhexanol in the presence of at least one stabilizer for acrylic acid, the esterification being catalyzed by sulphuric acid, to obtain a crude reaction mixture (B1) comprising 2-ethylhexyl acrylate, 2-ethylhexanol, acrylic acid, 2-ethylhexyl hydrogensulphate, traces of sulphuric acid and the usual impurities, which comprises: following the esterification, (a) adding to the crude reaction mixture (B1) a base in order to neutralize the acrylic acid, the 2-ethylhexyl hydrogensulphate and the traces of sulphuric acid which are present therein and to form an organic phase (O1) and an aqueous phase (A1), the resulting salts of the neutralization passing into the aqueous phase (A1), then separating the organic phase (O1) and the aqueous phase (A1) and recovering the 2-ethylhexyl acrylate from the organic phase (O1); wherein the aqueous phase of the process is stabilized, before or during the neutralization, by introducing at least one aqueous-phase stabilizer selected from the group consisting of: metal salts of Fe, Mn and Cu; 2,2,6,6-tetramethyl-1-piperidinyloxy (TEMPO); 4-hydroxy-2,2,6,6-tetramethyl-1-piperidinyloxy (4-hydroxy-TEMPO); 4-methoxy-2,2,6,6-tetramethyl-1-piperidinyloxy (4-methoxy-TEMPO); and 4-oxo-2,2,6,6-tetramethyl-1-piperidinyloxy (4-oxo-TEMPO); and (b) recovering the 2-ethylhexanol in (A1) from the aqueous phases.

3. A process according to claim 2, wherein the at least one aqueous-phase stabilizer is selected from the group consisting of the metal salts $CuSO_4$, $Fe_2(SO_4)_3$ and manganese acetate $Mn(Oac)_2$.

4. A process according to claim 2, wherein the at least one aqueous-phase stabilizer is introduced during the esterification and/or during the neutralization and/or between the esterification and neutralization.

5. A process according to claim 2, wherein the at least one aqueous-phase stabilizer is in a proportion of 20 to 1000 ppm with respect to the crude reaction mixture (B1).

6. A process according to claim 2, wherein the at least one stabilizer of acrylic acid is chosen from phenothiazine, hydroquinone methyl ether, di(tert-butyl)catechol, p-anilinophenol, paraphenylenediamine, hydroquinone and their mixtures in all proportions.

7. A process according to claim 2, wherein the at least one stabilizer of acrylic acid is present in a proportion of 200 to 2000 ppm with respect to the acrylic acid.

8. A process according to claim 3, wherein the at least one aqueous-phase stabilizer is introduced during the esterification and/or during the neutralization and/or between the esterification and neutralization.

9. A process according to claim 3, wherein the at least one aqueous-phase stabilizer is in a proportion of 20 to 1000 ppm with respect to the crude reaction mixture (B1).

10. A process according to claim 3, wherein the at least one stabilizer of acrylic acid is present in a proportion of 200 to 2000 ppm with respect to the acrylic acid.

11. A process according to claim 4, wherein the at least one stabilizer of acrylic acid is present in a proportion of 200 to 2000 ppm with respect to the acrylic acid.

12. A process according to claim 5, wherein the at least one stabilizer of acrylic acid is present in a proportion of 200 to 2000 ppm with respect to the acrylic acid.

13. A process according to claim 6, wherein the at least one stabilizer of acrylic acid is present in a proportion of 200 to 2000 ppm with respect to the acrylic acid.

14. A process according to claim 1, wherein hydroquinone is excluded from the stabilizing agent.

15. A process according to claim 14, wherein the stabilizing agent is selected from the group consisting of phenothiazine, hydroquinone methyl ether, di(tert-butyl) catechol, p-anilinophenol, paraphenylenediamine, hydroquinone and their mixtures in all proportions.

16. A process according to claim 15, wherein the stabilizing agent is present in a proportion of 200 to 2000 ppm with respect to the acrylic acid.

17. A process according to claim 1, wherein hydroquinone is contained in the stabilizing agent and the aqueous phase is stabilized before and/or during the neutralization.

18. A process according to claim 17, wherein the aqueous phase is stabilized with at least one aqueous-phase stabilizer selected from the group consisting of: metal salts of Fe, Mn and Cu; 2,2,6,6-tetramethyl-1-piperidinyloxy (TEMPO); 4-hydroxy-2,2,6,6-tetramethyl-1-piperidinyloxy (4-hydroxy-TEMPO); 4-methoxy-2,2,6,6-tetramethyl-1-piperidinyloxy (4-methoxy-TEMPO); and 4-oxo-2,2,6,6-tetramethyl-1-piperidinyloxy (4-oxo-TEMPO).

19. A process according to claim 17, wherein the aqueous phase is stabilized during the neutralization step.

20. A process according to claim 18, wherein the at least one aqueous-phase stabilizer is selected from the group consisting of: metal salts of Fe and Mn; 2,2,6,6-tetramethyl-1-piperidinyloxy (TEMPO); 4-hydroxy-2,2,6,6-tetramethyl-1-piperidinyloxy (4-hydroxy-TEMPO); 4-methoxy-2,2,6,6-tetramethyl-1-piperidinyloxy (4-methoxy-TEMPO); and 4-oxo-2,2,6,6-tetramethyl-1-piperidinyloxy (4-oxo-TEMPO).

* * * * *